(12) United States Patent
Zhang et al.

(10) Patent No.: US 7,384,397 B2
(45) Date of Patent: Jun. 10, 2008

(54) SYSTEM AND METHOD FOR SENSOR RECALIBRATION

(75) Inventors: Yanan Zhang, Valencia, CA (US); Lu Wang, Pasadena, CA (US); Rajiv Shah, Palos Verdes, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 679 days.

(21) Appl. No.: 10/751,327

(22) Filed: Dec. 30, 2003

(65) Prior Publication Data

US 2005/0143636 A1 Jun. 30, 2005

(51) Int. Cl.
*A61B 5/00* (2006.01)

(52) U.S. Cl. ...................... 600/365; 600/347

(58) Field of Classification Search ............... 205/775, 205/777.5; 600/309–367
See application file for complete search history.

(56) References Cited

U.S. PATENT DOCUMENTS

| | | | | |
|---|---|---|---|---|
| 6,275,717 | B1 * | 8/2001 | Gross et al. ............... | 600/345 |
| 6,387,048 | B1 | 5/2002 | Schulman et al. | |
| 2003/0153820 | A1 * | 8/2003 | Berner et al. ............... | 600/345 |
| 2003/0153821 | A1 | 8/2003 | Berner et al. | |
| 2003/0187338 | A1 | 10/2003 | Say et al. | |
| 2004/0019283 | A1 * | 1/2004 | Lambert et al. ............. | 600/476 |
| 2004/0220460 | A1 * | 11/2004 | Roberts ..................... | 600/333 |
| 2005/0109637 | A1 * | 5/2005 | Iyengar et al. ............. | 205/775 |
| 2005/0203358 | A1 * | 9/2005 | Monfre et al. ............. | 600/331 |
| 2007/0060811 | A1 * | 3/2007 | Roberts ..................... | 600/332 |

FOREIGN PATENT DOCUMENTS

WO   WO 98/58250   12/1998

OTHER PUBLICATIONS

PCT International Search Report as issued in International Application No. PCT/US2004/041856, Mailing date Apr. 13, 2005.

* cited by examiner

*Primary Examiner*—Robert L. Nasser, Jr.
*Assistant Examiner*—Karen E Toth
(74) *Attorney, Agent, or Firm*—Foley & Lardner LLP

(57) ABSTRACT

A system and method for calibrating a sensor. The method may include, without limitation, compiling an array of data relating to the sensor; adjusting a sensor parameter a first time based on data in the array; adjusting a curve representing the sensor output based on data in the array; and adjusting the sensor parameter a second time based on data in the array. The sensor may be an in vivo glucose sensor and the sensor parameter adjusted may be a current. The array may include historical as well as recent data, such as, for example, blood glucose readings and sensor electrode readings.

28 Claims, 7 Drawing Sheets a. Before Calibration b. After First Ig0 Adjustment c. After Curve Shape Adjustment d. After Second Ig0 Adjustment

SYSTEM AND METHOD FOR SENSOR RECALIBRATION

BACKGROUND

1. Field of the Invention

The present invention relates to recalibration techniques and, in particular, to recalibration techniques for implantable sensors.

2. Description of Related Art

The accuracy of a sensing system is generally limited by the drift characteristics of the sensing element over time and the amount of environmental noise introduced into the output of the sensing element. To accommodate the drift inherent in the sensing element and the noise inherent in the system environment, the sensing system is periodically calibrated, or recalibrated.

A typical recalibration routine is performed at regular intervals. Generally, a technician will measure an output of the sensing system in response to a known, accurate input. The sensing system is then adjusted, or recalibrated, so that the output of the sensing system matches that of the known, accurate input to within an acceptable error margin.

Typical recalibration routines are often inadequate for many sensing systems. Many sensing systems include sensing elements that exhibit non-linear outputs or outputs that change in a non-linear fashion over time. Thus, a simple linear adjustment during a recalibration procedure to force an output of the sensing system back to acceptable output values often fails to account for the true nature of many sensing elements. The result of simple linear adjustments may be a sensing system that is accurate only over a small range of the sensing elements capabilities or a sensing system that may not maintain acceptable levels of accuracy for extended periods of time.

SUMMARY

According to an embodiment of the present invention, method for calibrating a sensor may include compiling an array of data relating to the sensor; adjusting a sensor parameter a first time based on data in the array; adjusting a curve representing the sensor output based on data in the array; and adjusting the sensor parameter a second time based on data in the array. Also, the method may further include establishing a new sensor output based on the adjusted curve and the twice adjusted sensor parameter.

The array may include historical data and empirical data. The historical data may include measured blood glucose readings. The recent data may include blood glucose concentrations and electrode readings, such as, for example, glucose electrode readings and oxygen electrode readings.

According to embodiments of the present invention, adjusting a sensor parameter a first time may include adjusting a current. The current may be a nominal glucose current adjusted based on a shift of measured data points with respect to blood glucose readings. The shift may be a mean shift.

Adjusting the curve representing the sensor output may include performing a linear regression on data in the array. The result of the linear regression may determine a first calibration point. The first calibration point may be used to determine a plurality of calibration points.

According to an embodiment of the present invention, adjusting the curve representing the sensor output may include adjusting the curve in a piecewise linear fashion. The number of pieces in the piecewise linear adjustment may be five.

Adjusting a sensor parameter a second time may include adjusting a current. The current may be a nominal glucose current adjusted based on a shift of measured data points with respect to blood glucose readings. The shift may be a mean shift.

According to an embodiment of the present invention, an implantable sensing system may include a sensor for sensing a biological parameter; a processor connected to the sensor for processing the parameter; and a drug delivery unit connected to the processor for responding to the processor based on the parameter. The processor may be programmed to adjust an output of the sensor by compiling an array of data relating to the sensor; adjusting a sensor parameter a first time based on data in the array; adjusting a curve representing the sensor output based on data in the array; and adjusting the sensor parameter a second time based on data in the array.

The sensor may be a glucose sensor. The drug delivery unit may be an insulin pump. The insulin pump may deliver insulin in response to the sensed parameter.

According to embodiments of the present invention, a method for calibrating a sensor may include generating a calibration curve based on a priori empirical values; compiling a plurality of data values from the sensor; compiling independent historical values of a parameter sensed by the sensor; and reconciling the plurality of data values from the sensor to the calibration curve using the independent historical values. The sensor may be a glucose sensor. The independent historical values of a parameter sensed by the sensor may be metered blood glucose values.

Generating a calibration curve may include compiling a priori empirical values of sensors similar to the sensor being calibrated. Generating a calibration curve may also include generating a calibration curve representing a sensor having a plurality of phases.

Reconciling the plurality of data values may include adjusting an output current of the sensor. The output current of the sensor may be a nominal glucose current. Also, the nominal glucose current may be adjusted based on a shift of the plurality of data values from the sensor with respect to metered blood glucose values. Reconciling the plurality of data values may also include performing a linear regression on the plurality of data values. In addition, reconciling the plurality of data values may be performed in a piecewise linear fashion.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION

In the following description of embodiments of the invention, reference is made to the accompanying drawings which form a part hereof, and in which are shown by way of illustration specific embodiments in which the invention may be practiced. It is to be understood that other embodiments may be utilized and structural changes may be made without departing from the scope of the preferred embodiments of the present invention.

Embodiments of the present invention are directed to calibration techniques for use with implantable sensors that measure a characteristic of a patient's body. In preferred embodiments, the characteristic is the glucose level, and the implantable sensor is placed in an artery or a vein. Although embodiments of the present invention are primarily described in the context of glucose sensors used in the treatment of diabetes, the embodiments of the invention are applicable to a wide variety of patient treatment programs where a physiological characteristic is monitored. For example, embodiments of the invention can be used to determine the status and/or levels of a variety of characteristics including those associated with agents such as hormones, cholesterol, medication concentrations, pH, oxygen saturation, viral loads (e.g., HIV), or the like. Also embodiments of the present invention are not limited to implantation in an artery or vein, but can be implanted in and/or through subcutaneous, dermal, sub-dermal, inter-peritoneal or peritoneal tissue. Such sensors typically communicate a signal from the implantable sensor to either an internal or external monitor. The implantable sensor is primarily adapted for use with blood. However, still further embodiments of the implantable sensor may be used in other bodily fluids, such as interstitial fluid, spinal fluid, saliva, urine, tears, sweat, or the like.

Figure 1:
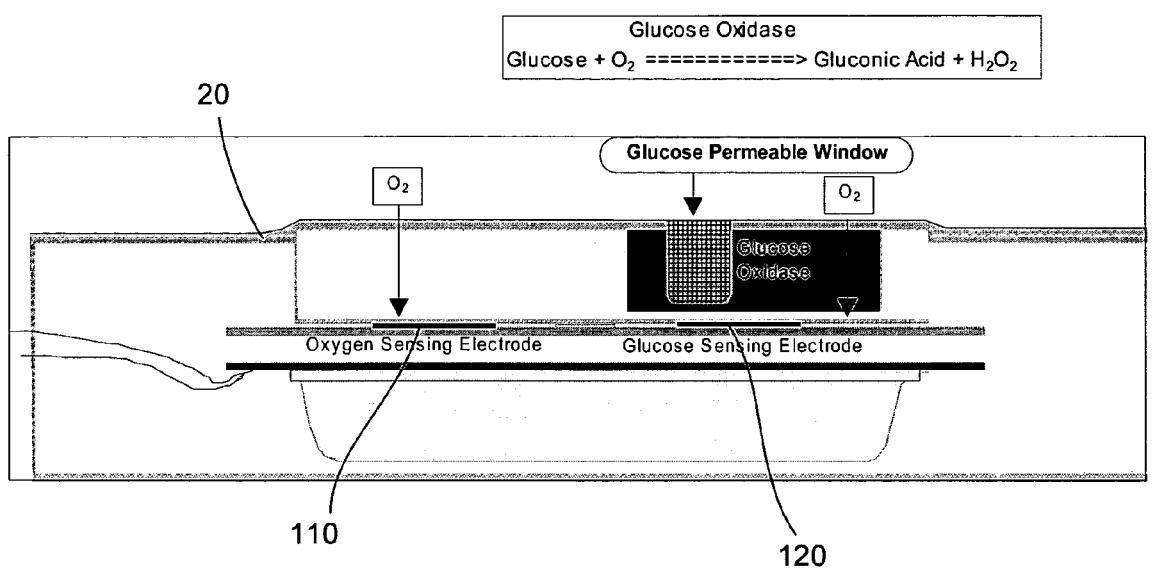
FIG. 1 shows a cross-sectional view of an exemplary sensor according to an embodiment of the present invention.

FIG. 1 is a cross-sectional view of an exemplary sensor in accordance with the embodiments of the present invention. The sensor generally includes, in one preferred form, an implantable enzyme electrode of the general type described in U.S. Pat. Nos. 4,650,547; 4,671,288; 4,781,798; 4,703,756; and 4,890,620, which are incorporated by reference herein. Such enzyme electrodes can be used in a sensor for direct contact with patient fluids, such as blood. In the preferred embodiments, a glucose oxygen sensor 20 is used to detect the level of glucose in the blood by measuring the depletion of oxygen as the glucose oxidase enzyme catalyzes a reaction between glucose and oxygen present in the blood according to the following reaction:

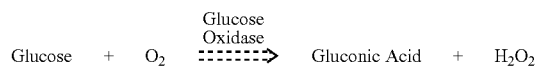

Typically, the glucose sensor 20 has at least two electrodes 110, 120 to detect the level of oxygen in the blood. Preferably, the first electrode is an oxygen sensing electrode 110 to detect the level of oxygen in the patient fluid (e.g. blood) as a reference point for the second electrode. The second electrode is a glucose sensing electrode 120 placed in the proximity of glucose oxidase to ascertain the oxygen depletion during the electrochemical reaction between oxygen and the glucose around the area of the glucose sensing electrode 120. The glucose oxygen sensor 20 is designed to send a particular current depending on the amount of oxygen present near the electrodes 110, 120. Given that the amount of current flowing to the electrodes has a fairly linear relationship the amount oxygen present in the area surrounding the electrodes 110, 120, a measurement of the currents can be used to determine the amount of glucose present in the blood, as described in application Ser. No. 10/034,338 entitled "Implantable Sensor Electrodes and Electronic Circuitry," filed on Dec. 28, 2001, which is incorporated by reference herein in its entirety.

In alternative embodiments, different sensors technology may be used, such as, but not limited to a hydrogen peroxide sensor or an optical sensor. A hydrogen peroxide sensor would work similar to an oxygen sensor, except that rather than measuring the amount of oxygen depleted in the presence of the glucose oxidase enzyme, the hydrogen peroxide sensor would measure the amount of hydrogen peroxide produced as a result of the reaction between oxygen and glucose in the presence of the glucose oxidase enzyme. Alternatively, an implantable optical sensor would include a photo-reactive substance or compound that optically changes, fluoresces, or the like, or other suitable compounds that detect changing properties in the presence of a bodily fluid analyte, such as glucose or the like. The compounds can also be used to detect the level of an analyte that has been ingested, injected or placed inside the body, such as marker substances, or the like. For example, possible compounds that produce a fluorescent change in the presence of a bodily fluid analyte are disclosed in U.S. Pat. No. 5,503,770 issued Apr. 2, 1996 to James et al. and entitled "Fluorescent Compound Suitable For Use In The Detection Of Saccharides"; U.S. Pat. No. 5,512,246 issued Apr. 30, 1996 to Russell et al. and entitled "Method and Means for Detecting Polyhydroxyl Compounds"; U.S. Provisional Application Ser. No. 60/007,515 to Van Antwerp et al. and entitled "Minimally Invasive Chemically Amplified Optical Glucose Sensor"; and U.S. Pat. No. 6,011,984 to Van Antwerp et al. and entitled "Detection of Biological Molecules Using Chemical Amplification", all of which are herein incorporated by reference. Other compounds using Donor Acceptor fluorescent techniques may be used, such as is disclosed in U.S. Pat. No. 5,628,310 issued May 13, 1997 to Rao et al. and entitled "Method and Apparatus to Perform Trans-cutaneous Analyte Monitoring"; U.S. Pat. No. 5,342,789 issued Aug. 30, 1994 to Chick et al. and entitled "Method and Device for Detecting and Quantifying Glucose in body Fluids"; and U.S. Pat. No. 5,246,867 issued Sep. 21, 1993 to Lakowicz et al. and entitled "Determination and Quantification of Saccharides by Luminescent Lifetimes and Energy Transfer", all of which are herein incorporated by reference.

Therefore, the generalized method for recalibration of a sensor according to an embodiment of the present invention may be applied to a variety of sensors, including, but not limited to, biological parameter sensors, physical parameter sensors and the like. For example, the generalized method may be applied to a variety of glucose sensors used in conjunction with implantable insulin pumps. Sensors and related systems of this type are disclosed in U.S. patent application Ser. No. 10/036,093, entitled, "Sensing Apparatus and Process," filed Dec. 28, 2001, and U.S. patent application Ser. No. 10/038,276, filed Jan. 2, 2002, entitled, "Sensor Substrate and Method of Fabricating Same," the contents of both of which are hereby incorporated by reference herein.

Sensors typically exhibit different characteristics during the useful life of the sensor. Specifically, sensors typically have three phases: (1) initialization phase, (2) stable phase, and (3) end of life phase. For example, after a sensor has been implanted into a patient, readings from the sensor needs to be adjusted for the first phase of the sensor life as the sensor becomes used to its environment. As the sensor begins to mature and the sensor enters its second phase of life, readings from the sensor need to be adjusted for its second phase of life. Lastly, as the sensor approaches its end of life and enters its third phase of life, the readings from the sensor need to be adjusted for its third phase of life. According to embodiments of the present invention, a calibration scheme is described which can be used to properly calibrate the sensor regardless of the phase of the sensor life and to identify which phase the sensor is in.

Figure 2:
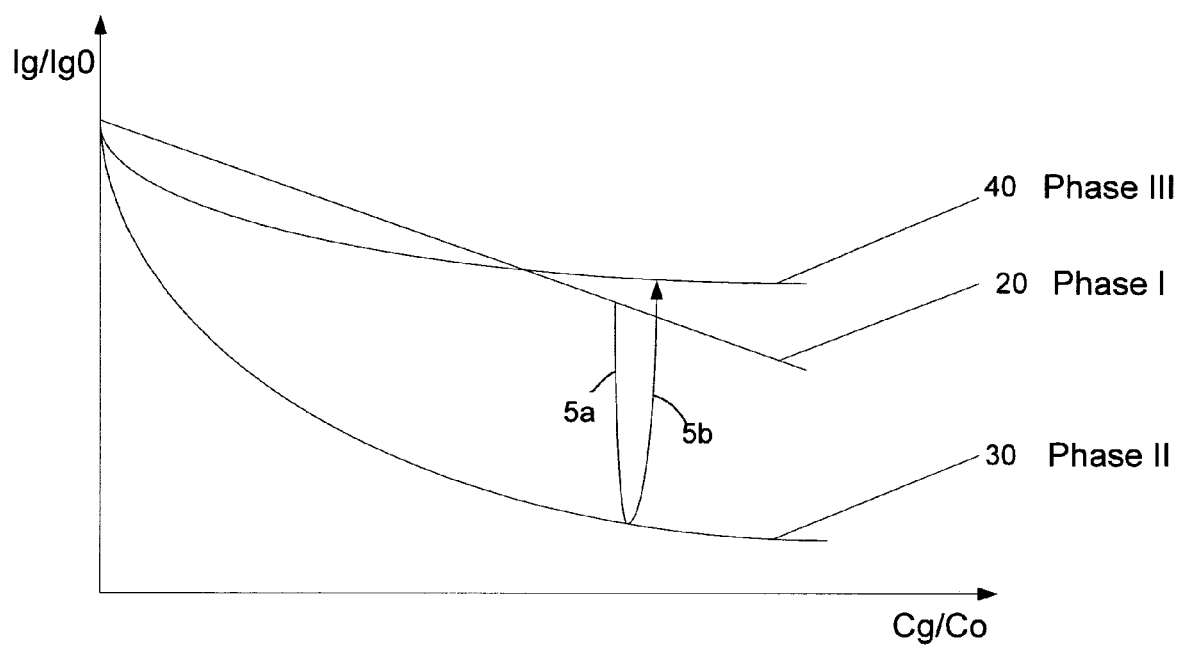
FIG. 2 shows a graph of a normalized calibration curve for the three phases of a sensor life according to an embodiment of the present invention.

According to embodiments of the present invention, a normalized calibration curve for the three phases of the sensor life is shown in FIG. 2. The curve shapes 20, 30, and 40 are the calibration curve shapes of each phase of the sensor life as determined based on empirical data collected from the use of sensors. Arrow 5a, 5b represent a typical life cycle of the calibration curves as the sensor changes from one phase to another phase, as will be described in greater detail below. Although the normalized calibration curves in FIG. 2 were originally derived based on glucose sensors, further research has proved that most sensors behave similarly and these calibration curves can be used with other type of sensors. According to embodiments of the present invention, sensor recalibrations will be performed not only based on independent characteristic values (e.g., blood meter values) but with use of the expected normalized calibration curves as will be described in greater detail below with respect to FIGS. 4 and 5.

In FIG. 2, the vertical axis, designated as $I_g/I_{g0}$, represents the ratio of real time glucose current to an imaginary glucose current in the absence of glucose. $I_g$ represents a sensor current output modulated by real time glucose measurements. $I_{g0}$ represents a nominal value of the sensor output current when no glucose is present for measurement. $I_{g0}$ can be calculated using the following formula:

$$I_{g0} = R*I_o,$$

where R is a conversion factor that is based on blood meter values to calibrate the sensor and $I_o$ is oxygen electrode output current. Since the presence of glucose lowers the glucose current, $I_g$ should never exceed $I_{g0}$. Therefore, the highest point along Y axis is 1, when $I_g = I_{g0}$. The horizontal axis, designated by $C_g/C_o$, represents the ratio of measured glucose concentration versus a nominal glucose concentration. $C_g$ represents the glucose concentration. $C_o$ may be calculated by multiplying a nominal sensor oxygen electrode output current $I_o$ by a constant. In other words, $$C_o = K \times I_o. \quad (1)$$

In equation (1), the value "K" is a constant based on the ratio of the oxygen concentration to the oxygen electrode current.

As described previously, phase 1 of the sensor's life may be viewed as a sensitivity period during the initial output of the sensor current with respect to glucose concentration. As can be seen in FIG. 2, line 20 is virtually completely linear during the first phase. This linearity represents the sensor output when it is initially placed in a patient. However, as the sensor stabilizes and enters phase 2, the current output of the sensor with respect to glucose concentration tends to become non-linear. The curve shape moves from line 20 to curve 30, as shown by the arrow 5a, as the sensor gets used to its environment and the enzyme or other mechanism on the sensor proceeds towards stabilization and settles into its environment.

The curve shift between line 20 and curve 30, represented by arrow 5a, represent a continuum of change in the sensor output current with respect to glucose concentration As the sensor finally stabilizes in its environment, it reaches a period of stabilization, represented by curve 30. According to embodiments of the present invention, the sensor may remain in this stabilized state for periods of one year or more.

Toward the end of the sensor life, the sensor output current tends to change less and less with respect to glucose concentration. Curve 30 moves toward curve 40 as represented by arrow 5b. Eventually, at the sensor's end of life, curve 40 is relatively flat for higher glucose concentrations, thereby rendering the sensor essentially ineffective for measurement. In other words, at the end of the sensor's life, the change in sensor output current with respect to a change in glucose concentration is minimal.

Figure 3:
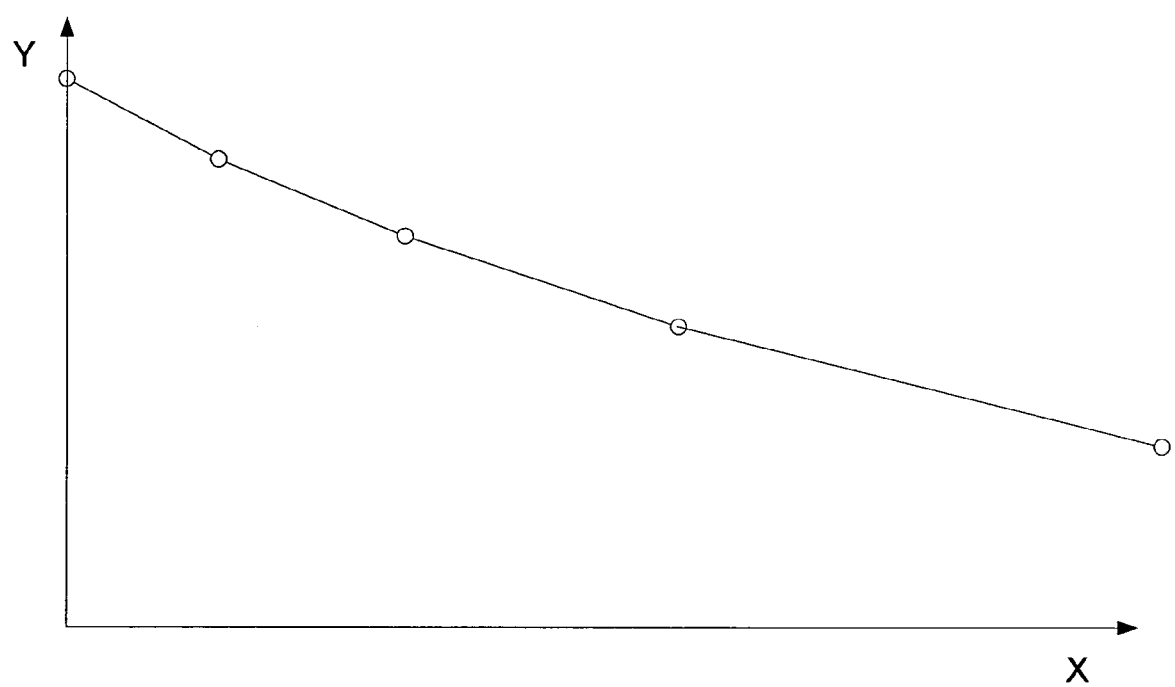
FIG. 3 shows a graph of a piecewise linear approximation technique for the calibration curve according to an embodiment of the present invention.

As described above, the present invention adjusts the calibration curve throughout the life of the sensor. Having a constantly updated calibration curve assures that accurate sensor readings are obtained regardless of the phase of the sensor. In further embodiments of the invention, a five-point piecewise linear approximation is used each time to approximate the calibration curve. In other words, instead of using a smooth curve, the curve is broken into five points and the line between each two consecutive points is assumed to be linear, as illustrated in FIG. 3. The piecewise linear approximation has been shown to reduce the complexity of the performed calculations while maintaining accurate results. In alternative embodiments, other mathematical approximations can be used to get the value of the calibration curve, including using a larger or smaller number of piecewise linear approximations.

Figure 4:
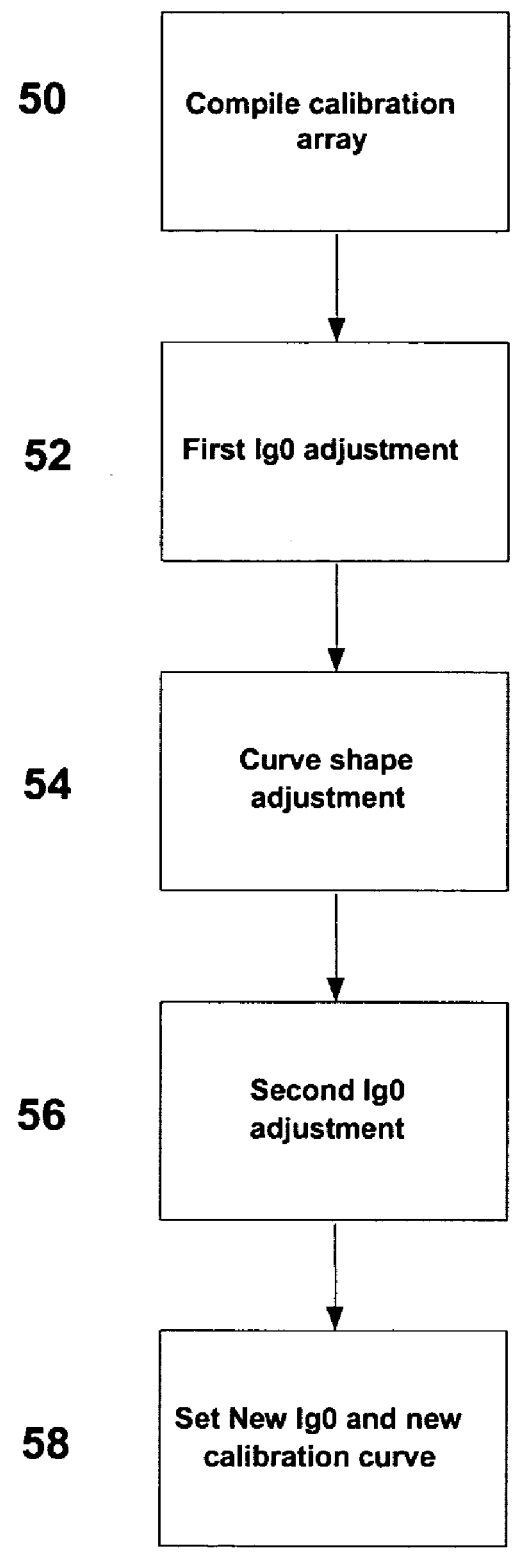
FIG. 4 shows a detailed method for calibrating a sensor according to an embodiment of the present invention.

FIG. 4 shows a more detailed method for calibrating a sensor according to an embodiment of the present invention. At Step 50, a calibration array is compiled from independent glucose readings, such as readings from a blood glucose meter taken simultaneously during the life of the sensor. The calibration array may be compiled from blood glucose meter readings, which have been taken and recorded for a particular sensor over a period of time, such as, for example, three weeks.

Each recalibration of the sensor uses historically measured glucose points and corresponding sensor data. The reference glucose points and corresponding sensor data may be placed into the calibration array. According to embodiments of the present invention, the calibration array may include the following elements: time, independently measured glucose points ($M_g$), measured blood glucose concentrations ($C_o$), glucose electrode readings ($I_g$) and oxygen electrode readings ($I_o$).

At Step 52, the nominal glucose current $I_{g0}$ may be adjusted. For example, under certain conditions it is possible that there may be a base line shift in the nominal glucose current, $I_{g0}$. Thus, the normalized nominal glucose current may not be exactly equal to "one." For the nominal glucose current adjustment, data may be used to adjust the current over a period of time. For example, according to an embodiment of the present invention, data over the last three weeks from the glucose sensor may be used to adjust the value of the nominal glucose current.

According to embodiments of the present invention, the nominal glucose current ($I_{g0}$) may be adjusted by calculating a shift of each measured data point with respect to the blood glucose meter readings. A mean shift may be determined and the value of the nominal glucose current adjusted accordingly, for example, either by adjusting the nominal glucose current by the amount of the mean shift or by adjusting the nominal glucose current by an amount corresponding to or dependent upon the mean shift. To calculate the mean shift, the shift to the calibration curve in the y-direction, the coordinates, $X_m$ and $Y_m$, may be calculated as follows:

$$X_m = M_g(t)/C_o(t+a) \quad (2)$$

$$Y_m = I_g(t+a)/(R \cdot I_o(t+a)) \quad (3)$$

$X_m$ and $Y_m$ represent the x-y coordinates to map the meter values to the calibration curve graph. The constant a is an empirically derived time shift to correlate the sensor reading with the blood glucose meter. The time shift, a, has been found to be approximately 15 minutes.

Y_shift=$Y_m/Y_c$, in which $Y_c$ is the corresponding point on the calibration curve with the same $X_m$ value. In the first $I_{g0}$ adjustment (i.e. step 52), the Y_shift is calculated for only the $Y_m$ and $X_m$ values corresponding to glucose values less than 120 mg/dl. The mean shift of $I_{g0}$ is then calculated by:

$$\text{mean\_shift} = \Sigma(Y\_shift)/N,$$

where N is the total number of calibration points (i.e., meter readings).

Once the mean shift has been determined, the value "R" may be adjusted as follows:

$$R' = R \cdot \text{mean shift} \quad (4)$$

Once the new value of R is calculated, the $Y_m$ values of each calibration point may be adjustment according to the new value of R:

$$Y_m' = I_g(t+a)/(R' \cdot I_o(t+a))$$

Thus, adjusting the nominal glucose current effectively changes the value of "R" in equation (4), above. Once the new $Y_m$ ($Y_m'$) is determined, adjustment on the shape of the calibration curve can be determined.

At Step 54, adjustments may be made to the shape of the measured curve, i.e., the shape of the sensor calibration curve. The adjustments to the calibration curve may be used to provide calculation of the sensor output.

The difference between the new $Y_m$ ($Y_m'$) is then calculated and the result is stored in array $Y_d$ such that $Y_d = Y_m' - Y_c$.

$Y_d$ is then regressed against the corresponding x coordinates, $X_m$, by performing a standard weighted linear regression. The slope and intercept of the regression results may be calculated as follows:

$$\text{Slope} = \frac{\left(\sum w_i\right)\left(\sum w_i x_i Y d_i\right) - \left(\sum w_i x_i\right)\left(\sum w_i Y d_i\right)}{\Delta} \quad (6)$$

$$\text{Intercept} = \frac{\left(\sum w_i x_i^2\right)\left(\sum w_i Y d_i\right) - \left(\sum w_i x_i\right)\left(\sum w_i x_i Y d_i\right)}{\Delta} \quad (7)$$

where $$\Delta = \left(\sum w_i\right)\left(\sum w_i x_i^2\right) - \left(\sum w_i x_i\right)^2$$

The weights, $w_i$, are determined according to the time at which that glucose measurement point is taken. According to an embodiment of the present invention, the weight declines linearly as the reference point is further back in history from the time the calibration:

$$w_i = (T-i),$$

in which T is the time of calibration and i is the time at which the glucose measurement point is taken.

The result of the linear regression is used to determine the last recalibration point. The last recalibration point is one of the five points on the calibration curve corresponding to the highest glucose concentration. The last calibration point, Y(5), is determined as follows:

$$Y(5) = Y(5) + \text{slope} \cdot X(4) + \text{Intercept}.$$

The slope and intercept are determined by equations 6 and 7.

The remaining calibration points can then be determined as follows:

$$\Delta Y(i)/(1-y(i)) = H \cdot \Delta Y(i+1)/(1-y(i+1))$$

in which $\Delta Y$ is the amount of change for calibration point Y and the variable H is set to 0.9 if the sensor is gaining sensitivity and 0.7 when the sensor losing sensitivity. The variable H may be different in different phases of sensor life.

The new calibration curve, therefore, becomes:

$$Y(i) = Y(i) + \Delta Y(i)$$

Once the new curve shape is determined, a second $I_{g0}$ adjustment can be made to ensure the maximum accuracy. The second $I_{g0}$ adjustment is identical to the first $I_{g0}$ adjustment, except that all calibration points, as opposed to only the low glucose value points (i.e., $Y_m$ and $X_m$ coordinates corresponding to glucose values under 120 mg/dl), will be used. At Step 58, a new nominal glucose current and new calibration curve may be set for the sensor. Thus, after recalibration, the sensor output can be calculated using the new calibration curve derived from the recalibration procedure of FIG. 4.

Figure 5A:
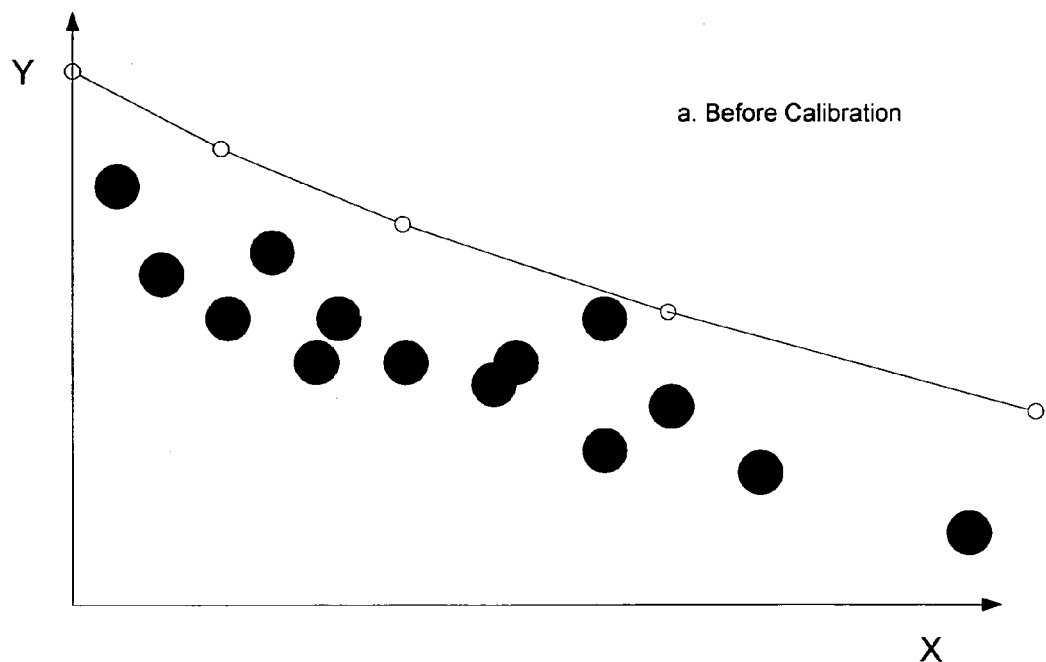
FIG. 5a-d shows a resulting adjustment of a recalibrated sensor output according to an embodiment of the present invention.
Figure 5B:
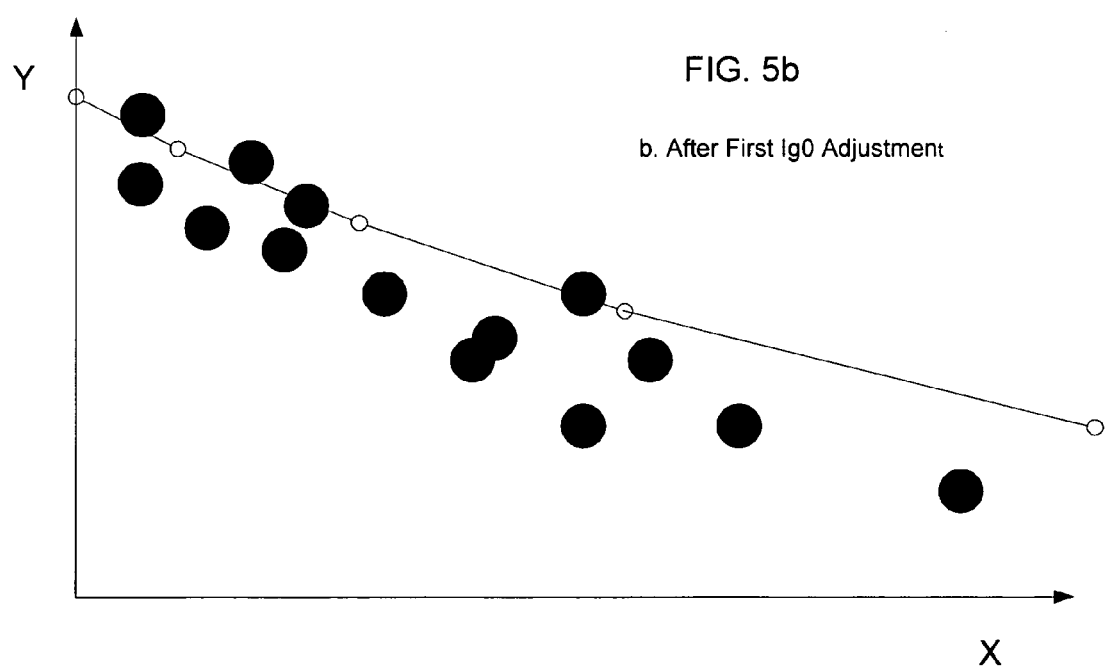
Figure 5C:
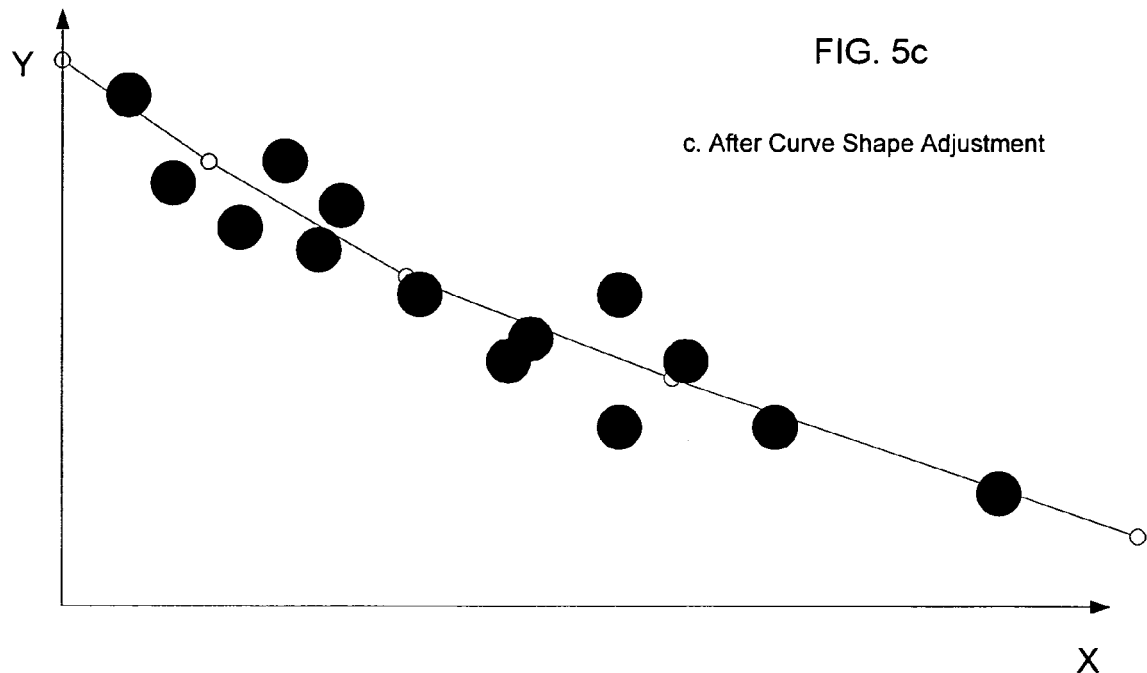
Figure 5D:
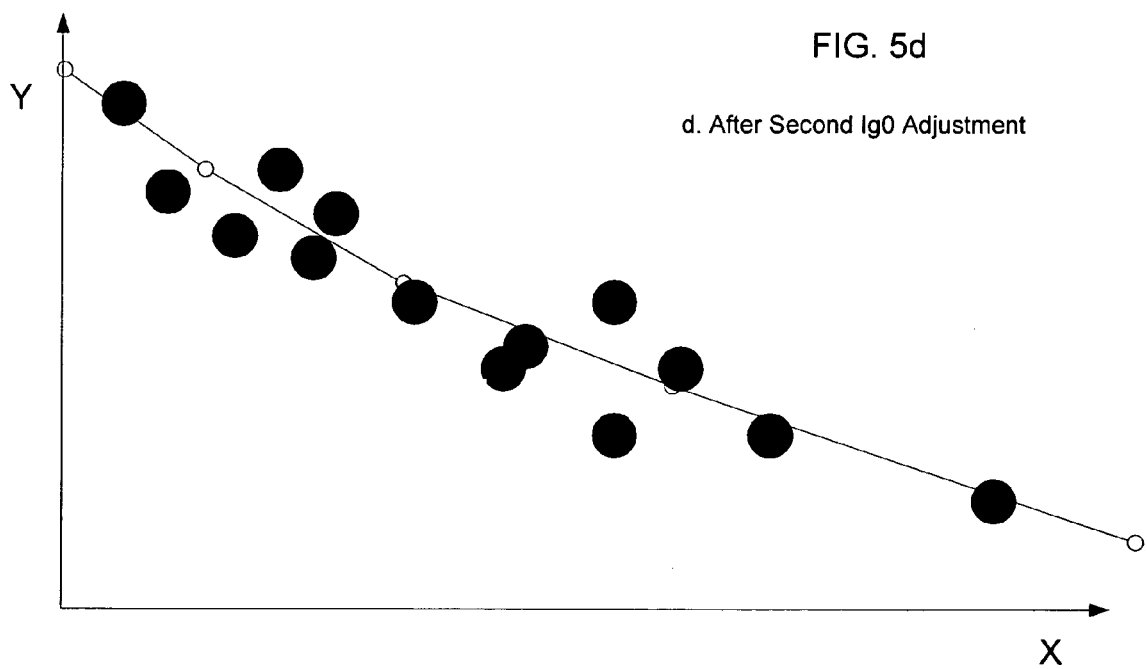

FIGS. 5*a-d* summarize the step-by-step change of the calibration curve. FIG. 5*a* shows the calibration curve before the recalibration. The reference points mapped on the calibration graph are significantly deviant from the calibration curve. In FIG. 5*b*, the sensor has undergone first $I_{g0}$ adjustment; the low end points are lined up with the new calibration curve. In FIG. 5*c*, the sensor has undergone curve shape adjustment, and the high-end points are also lined up with the calibration curve. In FIG. 5*d*, the sensor has undergone the second $I_{g0}$ adjustment for fine tuning purposes. As seen in FIG. 5*d*, the curve is likely to change only slightly with respect to the reference points during the second $I_{g0}$ adjustment. In alternative embodiments, a second $I_{g0}$ adjustment may be omitted if fine tuning of the calibration curve is deemed unnecessary or additional $I_{g0}$ adjustments may be performed if further fine tuning is deemed needed.

Figure 6:
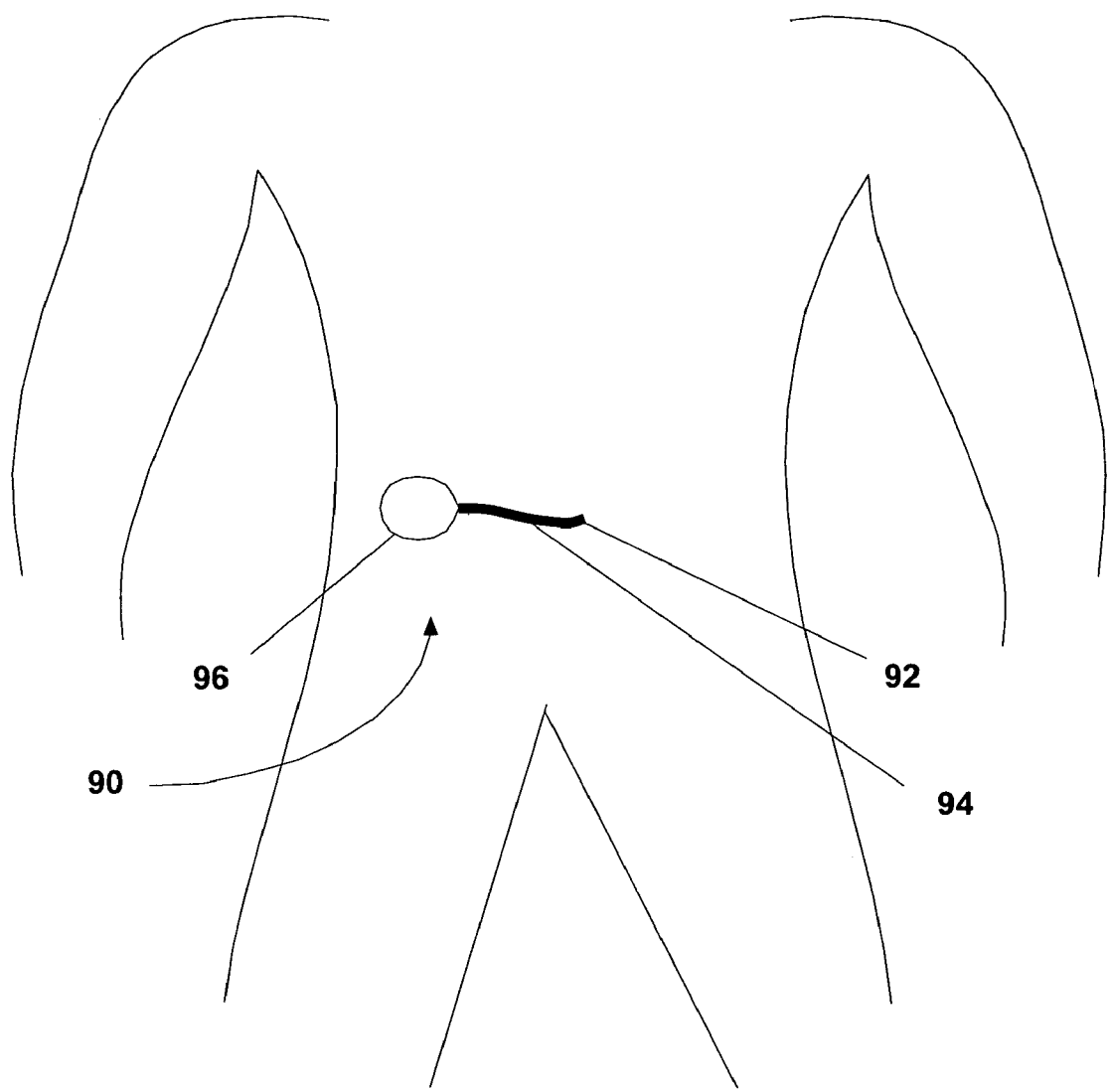
FIG. 6 shows an implanted sensing system in which embodiments of the invention may be used according to embodiments of the present invention.

FIG. 6 shows an implanted sensing system in which embodiments of the present invention may be used. In FIG. 6, an implanted sensing system 90 may include, but is not limited to, a pump 96, a catheter 94 having one end attached to the pump 96, and a sensor 92 disposed at another end of the catheter 94. The pump 96 may be an insulin pump and the sensor 92 may be a glucose sensor. The sensor 92 may be calibrated using embodiments of the present invention. A properly calibrated sensor 92 may send signals to the pump 96, enabling the pump 96 to accurately deliver medication or other fluids, such as insulin, for example, through the catheter 94 to a patient.

Thus, according to embodiments of the present invention, a non-linear curve may be adjusted using a linear regression. Using a linear regression rather than a non-linear regression provides many advantages. For example, the amount of processing power saved by using a linear regression rather than a non-linear regression is dramatic. Processing power is critical in battery operated or otherwise powered implantable systems. Moreover, linear regressions are far more stable than non-linear regressions when input data varies widely. Stability is critical in medical diagnostic and treatment systems such as an implantable insulin pump, for example.

While particular embodiments of the present invention have been shown and described, it will be obvious to those skilled in the art that the invention is not limited to the particular embodiments shown and described and that changes and modifications may be made without departing from the spirit and scope of the appended claims. Thus, embodiments of the present invention may be used to recalibrate any sensor that exhibits nonlinear characteristics. Generally, embodiments of the present invention may be adapted for use with any type of sensor in any type of environment where calibration of the sensor over its lifetime is desired.

What is claimed is:

1. A method for adjusting a calibrating curve for a sensor calibration comprising:
   compiling a calibration array of data values relating to the sensor;
   generating a calibration curve;
   adjusting a nominal output current of the sensor based on data in the calibration array;
   adjusting the calibration curve based on the adjusted value of the nominal output current;
   wherein adjusting the calibration curve representing the sensor output further comprises performing a linear regression on data in the calibration array; and
   wherein a result of the linear regression determines a first calibration point.

2. The method of claim 1, wherein compiling the calibration array comprises compiling historical data.

3. The method of claim 2, wherein the historical data comprises measured blood glucose readings.

4. The method of claim 1, wherein compiling the calibration array comprises compiling recent data.

5. The method of claim 4, wherein the recent data comprises electrode readings.

6. The method of claim 5, wherein the electrode readings comprise glucose electrode readings and oxygen electrode readings.

7. The method of claim 4, wherein the recent data comprises measured blood glucose concentrations.

8. The method of claim 7, wherein the nominal output current is a nominal glucose current.

9. The method of claim 8, wherein the nominal glucose current is adjusted based on a shift of measured data points with respect to blood glucose readings.

10. The method of claim 9, wherein the shift is a mean shift.

11. The method of claim 1, wherein the first calibration point is used to determine a plurality of calibration points.

12. The method of claim 1, wherein adjusting the calibration curve representing the sensor output comprises adjusting the calibration curve in a piecewise linear fashion.

13. The method of claim 12, wherein a number of pieces in the piecewise linear adjustment is five.

14. The method of claim 1, further comprising compiling a second calibration array of data values relating to the sensor; adjusting the nominal output current of the sensor a second time based on data in the second calibration array.

15. The method of claim 14, wherein the nominal output current is a nominal glucose current.

16. The method of claim 15, wherein the nominal glucose current is adjusted based on a shift of measured data points with respect to blood glucose readings.

17. The method of claim 16, wherein the shift is a mean shift.

18. The method of claim 1, further comprising establishing a new sensor output based on the adjusted calibration curve and the twice adjusted nominal output current.

19. The method of claim 1, wherein generating a calibration curve comprises generating a calibration curve based on a priori empirical values, and wherein the method further comprises:
   compiling a plurality of data values from the sensor;
   compiling independent historical values of a parameter sensed by the sensor; and
   reconciling the plurality of data values from the sensor to the calibration curve using the independent historical values.

20. The method of claim 19, wherein the sensor is a glucose sensor.

21. The method of claim 19, wherein generating a calibration curve comprises compiling a priori empirical values of sensors similar to the sensor being calibrated.

22. The method of claim 19, wherein generating a calibration curve comprises generating a calibration curve representing a sensor having a plurality of phases.

23. The method of claim 19, wherein the independent historical values of a parameter sensed by the sensor are metered blood glucose values.

24. The method of claim 19, wherein reconciling the plurality of data values comprises adjusting an output current of the sensor.

25. The method of claim 24, wherein the output current of the sensor is a nominal glucose current.

26. The method of claim 25, wherein the nominal glucose current is adjusted based on a shift of the plurality of data values from the sensor with respect to metered blood glucose values.

27. The method of claim 19, wherein reconciling the plurality of data values comprises performing a linear regression on the plurality of data values.

28. The method of claim 19, wherein reconciling the plurality of data values is performed in a piecewise linear fashion.

* * * * *